(12) United States Patent
Dale et al.

(10) Patent No.: US 8,535,924 B2
(45) Date of Patent: *Sep. 17, 2013

(54) GRANULES WITH REDUCED DUST POTENTIAL COMPRISING AN ANTIFOAM AGENT

(75) Inventors: Douglas A. Dale, Pacifica, CA (US); Thomas S. Green, Montara, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/288,680

(22) Filed: Nov. 3, 2011

(65) Prior Publication Data

US 2012/0114948 A1    May 10, 2012

Related U.S. Application Data

(63) Continuation of application No. 10/113,994, filed on Apr. 1, 2002, now Pat. No. 8,076,113.

(60) Provisional application No. 60/281,108, filed on Apr. 2, 2001.

(51) Int. Cl.
| | |
|---|---|
| *C12N 9/98* | (2006.01) |
| *C12N 11/18* | (2006.01) |
| *C12N 11/14* | (2006.01) |
| *C12N 11/02* | (2006.01) |
| *C12N 11/08* | (2006.01) |
| *C12N 11/04* | (2006.01) |
| *D06M 16/00* | (2006.01) |
| *C11D 7/42* | (2006.01) |
| *C11D 3/386* | (2006.01) |

(52) U.S. Cl.
USPC ........... 435/187; 435/175; 435/176; 435/177; 435/180; 435/182; 435/264; 510/320; 510/530

(58) Field of Classification Search
None
See application file for complete search history.

(56) References Cited

U.S. PATENT DOCUMENTS

| | | | |
|---|---|---|---|
| 4,106,991 | A | 8/1978 | Markussen et al. |
| 4,610,761 | A | 9/1986 | Eklund et al. |
| 4,673,527 | A | 6/1987 | Goudy, Jr. et al. |
| 4,689,297 | A | 8/1987 | Good et al. |
| 4,740,469 | A | 4/1988 | Nishinaka et al. |
| 4,760,025 | A | 7/1988 | Estell et al. |
| 5,053,274 | A | 10/1991 | Jones |
| 5,227,084 | A | 7/1993 | Martens et al. |
| 5,254,283 | A | 10/1993 | Arnold et al. |
| 5,324,649 | A | 6/1994 | Arnold et al. |
| 5,431,847 | A | 7/1995 | Winston et al. |
| 5,739,091 | A | 4/1998 | Kiesser et al. |
| 5,879,920 | A | 3/1999 | Dale et al. |
| 6,310,027 | B1 | 10/2001 | Dale |
| 6,322,818 | B1 | 11/2001 | Rebler |
| 6,328,967 | B1 | 12/2001 | Rivera |
| 8,076,113 | B2 * | 12/2011 | Dale et al. ................. 435/187 |

FOREIGN PATENT DOCUMENTS

| | | |
|---|---|---|
| EP | 0 130 756 B1 | 2/1991 |
| EP | 0 716 144 A2 | 6/1996 |
| EP | 1 072 612 A1 | 1/2001 |
| WO | WO 90/09440 | 8/1990 |
| WO | WO 91/06637 | 5/1991 |
| WO | WO 91/09941 | 7/1991 |
| WO | WO 93/07263 | 4/1993 |
| WO | WO 97/12958 | 4/1997 |
| WO | WO 99/32613 A1 | 7/1999 |
| WO | WO 00/29534 A1 | 5/2000 |
| WO | WO 01/60916 A1 | 8/2001 |

OTHER PUBLICATIONS

Ghildyal,k, N.P. et al., "Foam Control in submerged Fermentation: State of the Art," *Advances in Applied Microbiology*, vol. 33, pp. 173-222, 1988.

Vardar-Sukan, F., "Foaming and Its Control in Bioprocesses," *Recent Advances in Biotechnology*, pp. 113-146, 1992.

\* cited by examiner

*Primary Examiner* — David M Naff
(74) *Attorney, Agent, or Firm* — Danisco US Inc.

(57) ABSTRACT

A granule with an allergenic component has reduced dust by including antifoam added during the production of the granule. The antifoam may be dispersed throughout the granule or added to one of the components of the granule. The granule with antifoam produces at least 30% less dust than a comparable granule produced according to a process in which no antifoam is added.

18 Claims, No Drawings

GRANULES WITH REDUCED DUST POTENTIAL COMPRISING AN ANTIFOAM AGENT

RELATED APPLICATIONS

This application is a continuation application claiming priority to U.S. patent application Ser. No. 10/113,994, which was filed Apr. 1, 2002, now U.S. Pat. No. 8,076,113, which claimed priority to U.S. Provisional Applications 60/281,108, filed Apr. 2, 2001. The disclosures of the priority applications are incorporated by reference in their entirety.

BACKGROUND OF THE INVENTION

Recently the use of enzymes, especially of microbial origin, has become more and more common. Enzymes are used in several industries including, for example, the starch industry, the dairy industry, and the detergent industry. It is well known in the detergent industry that the use of enzymes, particularly proteolytic enzymes, has created industrial hygiene concerns for detergent factory workers, particularly due to the health risks associated with dustiness of the available enzymes.

Since the introduction of enzymes into the detergent business, many developments in the granulation and coating of enzymes have been offered by the industry. See for example the following patents relating to enzyme granulation:

U.S. Pat. No. 4,106,991 describes an improved formation of enzyme granules by including within the composition undergoing granulation, finely divided cellulose fibers in an amount of 2-40% w/w based on the dry weight of the whole composition. In addition, this patent describes that waxy substances can be used to coat the particles of the granulate.

U.S. Pat. No. 4,689,297 describes enzyme containing particles which comprise a particulate, water dispersible core which is 150-2,000 microns in its longest dimension, a uniform layer of enzyme around the core particle which amounts to 10%-35% by weight of the weight of the core particle, and a layer of macro-molecular, film-forming, water soluble or dispersible coating agent uniformly surrounding the enzyme layer wherein the combination of enzyme and coating agent is from 25-55% of the weight of the core particle. The core material described in this patent includes clay, a sugar crystal enclosed in layers of corn starch which is coated with a layer of dextrin, agglomerated potato starch, particulate salt, agglomerated trisodium citrate, pan crystallized NaCl flakes, bentonite granules or prills, granules containing bentonite, Kaolin and diatomaceous earth or sodium citrate crystals. The film forming material may be a fatty acid ester, an alkoxylated alcohol, a polyvinyl alcohol or an ethoxylated alkylphenol.

U.S. Pat. No. 4,740,469 describes an enzyme granular composition consisting essentially of from 1-35% by weight of an enzyme and from 0.5-30% by weight of a synthetic fibrous material having an average length of from 100-500 micron and a fineness in the range of from 0.05-0.7 denier, with the balance being an extender or filler. The granular composition may further comprise a molten waxy material, such as polyethylene glycol, and optionally a colorant such as titanium dioxide.

U.S. Pat. No. 5,254,283 describes a particulate material which has been coated with a continuous layer of a non-water soluble, warp size polymer. U.S. Pat. No. 5,324,649 describes enzyme-containing granules having a core, an enzyme layer and an outer coating layer. The enzyme layer and, optionally, the core and outer coating layer contain a vinyl polymer.

WO 91/09941 describes an enzyme containing preparation whereby at least 50% of the enzymatic activity is present in the preparation as enzyme crystals. The preparation can be either a slurry or a granulate.

WO 97/12958 discloses a microgranular enzyme composition. The granules are made by fluid-bed agglomeration which results in granules with numerous carrier or seed particles coated with enzyme and bound together by a binder.

However, even in light of these developments offered by the industry (as described above) there is a continuing need for low-dust granules. In particular, it is especially problematic in the detergent industry when granules in general, or those comprising proteins or enzymes, form dust and are aerosolized. In these cases, workers are often exposed to the contents of the granules and can develop severe allergic reactions. Therefore, it is an object of the present invention to provide a method of producing a low-dust enzyme granule by adding antifoam agent. It is a further object of the invention to facilitate a safer environment for workers in the detergent industry who are exposed to enzyme containing granules.

SUMMARY OF THE INVENTION

The present invention relates to a granule that has a reduced dusting potential. The granule of the invention is prepared in a process in which an antifoam agent is added during granule manufacture such that the antifoam agent is present in the resulting granule in a concentration sufficient to reduce the dusting potential of the produced granule.

In one embodiment of the invention, a granule for use in solid formulations comprises a seed particle; an admixture of an allergenic agent and antifoaming agent surrounding the seed particle; wherein the granule has at least 10% less dust as measured by a Heubach test than a granule without the antifoaming agent prepared by a similar process.

In another embodiment of the invention, a granule for use in solid formulations comprises a seed particle; an admixture of an allergenic component and antifoaming agent surrounding the seed particle; a coating surrounding the admixture, the coating comprising an antifoaming agent and at least one barrier material, wherein the granule has at least 10% less dust as measured by a Heubach test than a granule without the antifoaming agent prepared by a similar process.

In yet another embodiment of the invention, a granule for use in solid formulations comprises a seed particle; an allergenic component surrounding the seed particle; a coating surrounding the allergenic component, the coating comprising at least one barrier material, and an outer coating comprising at least an anti-foaming agent, wherein the granule has at least 10% less dust as measured by a Heubach test than a granule without the antifoaming agent prepared by a similar process.

Another embodiment is a method of producing the above granules. The granules are produced by preparing a mixture of compounds, including an allergenic component to be incorporated into a granule; adding an antifoam agent to the mixture; and using the mixture comprising the antifoam to form a granule or a layer thereof. In another embodiment of producing the granules, the antifoam agent is mixed with the allergenic component. In yet another embodiment of the method, the antifoam agent also is mixed with a barrier layer which surrounds the allergenic component. In yet another embodiment of the method, the antifoam agent is added only to a coating that surrounds a barrier layer over the allergenic component.

DETAILED DESCRIPTION OF THE INVENTION

The present invention provides a granule with decreased dust production. The granule is produced by a process that includes the addition of an antifoaming agent. The invention includes any process in which antifoam is added such that a resultant granule produces decreased dust as compared with a granule prepared in a process without antifoam added.

As pointed out above, a critical issue in the use of enzymes in many consumer or industrial applications arises from the fact that enzymes are often potential allergens. Accordingly, a need exists for enzyme granules to be formulated so as to minimize the risk of sensitization and allergic reaction on the part of factory workers who are exposed to enzymes as raw materials, for example in laundry detergent manufacturing factories, and also on the part of the general public which may be exposed to enzyme containing granules in consumer products. Manufacturing operations such as conveying, sieving, blending, and filling can exert attritional forces on enzyme granules which have a tendency to cause breakage of granules and liberation of enzymes which can then form airborne dusts or aerosols. Significant efforts involving various granulation and encapsulation technologies have been directed towards minimizing the potential of enzyme granules to form such allergenic dusts. For example, U.S. Pat. No. 4,106,991 (Markussen) describes the use of cellulose fibers and binders in a drum granulator to produce a tougher, more attrition resistant granule. Similarly, PCT Publication No. WO 93/07263 (Genencor) describes a process for making a superior low dust granule in a fluidized bed spray-coater, comprising a core, an enzyme layer and an outer coating layer, by utilizing polyvinyl alcohol as a binder and coating agent.

As used herein, the term "dust" refers to the tendency of a granule, upon degradation or breaking of the granule structure, to liberate fine airborne particulates. Granule dust is routinely measured in the industry. For example, granule dust can be measured by several different techniques, each technique being well suited for specific conditions and not necessarily being interchangeable. However, two techniques in common use within the enzyme industry have been validated for their ability to predict the actual tendency of mechanically weaker granules to release higher levels of enzyme into the air in detergent manufacturing plants.

Two enzyme dust test methods which provide excellent predictive results include the Elutriation Test and the Heubach Attrition Test. Each of these tests is well known in the industry. However, for the convenience of the reader, the tests are briefly summarized as follows. In the Elutriation Test, 60 grams of enzyme granules are place on a porous glass frit at the bottom of a tall glass tube and fluidized with a constant dry airstream at 0.8 m/s for a period of 20 to 40 minutes. In the Heubach Attrition Test, 13.5 grams of granules are placed in a small, cylindrical chamber fitted with a rotating paddle and four stainless steel balls, which rotate while dust particles are stripped from the moving bed of granules by an airstream for 20 minutes. In both methods, the dust particles stripped off by the airstream are deposited on an external filter pad, which is subsequently assayed gravimetrically for its total weight ("total dust") or assayed biochemically for its active "enzyme dust". While these methods have been found useful by the Applicants, one of skill in the art will recognize that suitable methods of dust determination include any reliable method for reproducibly subjecting enzyme granules to forces which result in granule breakage or attrition.

Preferably, the granule of the invention produces at least 20% less dust, more preferably at least 40% less dust, even more preferably at least 60% less dust and even more preferably at least 80% less dust, and most preferably at least 90% less dust than a comparable granule made according to an identical process but for the lack of added antifoam being present in the resulting granule.

As used herein, "antifoam" or "antifoam agent" means compounds routinely used to prevent or break foam in industrial applications. These can also be referred to as defoamers, or defoaming agents. These compounds are surface active substances which decrease the surface elasticity of liquids and prevent metastable foam formation. The foam breaks as a result of the tendency to attain the equilibrium between the surface elasticity of the liquid and the surface active substances. (Vardar-Sukan, Recent Adv. Biotechnol. (1991), pp. 113-146). A number of compounds find application as antifoam agents, including fats, oils, waxes, aliphatic acids or esters, alcohols, sulfates, sulfonates, fatty acids, soaps, nitrogenous compounds, phosphates, polyglycols, sulfides, thio compounds, siloxanes and halagenated and inorganic compounds (Ghildyal, Adv. Appl. Microbiol. (1988), vol. 33, pp. 173-222). Preferably, the antifoam used is consistent with use in a bioprocess. Particularly, oils, fatty acids, esters, polyglycols and siloxanes are useful. Most preferably, the inventors herein have determined that an excellent antifoam agent is ethylene oxide propylene oxide co-polymer. An example of an ethylene-oxide propylene-oxide co-polymer having an approximate molecular weight of 2200 is Mazu™, available commercially from Mazer Chemicals, Inc.

According to a preferred embodiment of the invention, the amount of antifoam added is sufficient to significantly reduce the dust potential of the resulting granule. Preferably, the antifoam is added in a quantity which results in a weight percentage in the final granule equal to between about 0.25% and 10% w/w; more preferably between 0.35% and 5% w/w and most preferably between 0.5% and 2% w/w.

The antifoam agent may be added during any step of the process towards the production of a granule. Accordingly, the antifoam may be added to the enzyme fermentation broth, during a step involving recovery or purification of enzyme, as a constituent in any formula related to the granule or a layer of a granule. As one of skill in the art will readily recognize, antifoam agent can be added at numerous different steps of the granule production process, the best method depending on the specific granule production process. Thus, the present invention is not intended to be limited to any specific type of granule or granule production method but is capable of numerous modifications or variations of the methods described below.

In a preferred embodiment of the invention, the granule is a layered granule in which different layers comprise different constituents intended for a various benefits or effects. In a typical layered granule, as described in more detail below, it is possible to include any of a number of layers. For example, the seed or core may be coated with any combination of bleach layers, barrier layers, coating layers, enzyme or other protein layers and other protective or active layers.

In one embodiment, the composition of the invention is formed by the production of a particulate, or core, about a small seed or carrier particle. A seed or carrier particle is an inert particle upon which a further material (along with a binder and, optionally, one or more proteins such as enzymes) can be deposited (e.g., coated, layered, etc.). Suitable seed materials include inorganic salts, sugars, sugar alcohols, small organic molecules such as organic acids or salts, minerals such as clays or silicates or a combination of two or more of these. Suitable soluble ingredients for incorporation into seed particles include sodium chloride, potassium chloride, ammonium sulfate, sodium sulfate, sodium sesquicarbonate, urea, citric acid, citrate, sorbitol, mannitol, oleate, sucrose, lactose and the like. Soluble ingredients can be combined with dispersible ingredients such as talc, kaolin or bentonite. Seed particles can be fabricated by a variety of granulation techniques including: crystallization, precipitation, pan-coating, fluid-bed coating, fluid-bed agglomeration, rotary atomization, extrusion, prilling, spheronization, drum granulation and/or high shear agglomeration. In the particulates of the present invention, if a seed particle is used, then the ratio of seed particles to particulates is 1:1 to 1:4 wt/wt. Similarly, in the granules of the present invention, the ratio of cores to granules also is 1:1 to 1:4 wt/wt. Preferably, the seed particle delivers acceptable strength while not adversely affecting the density of the final core or granule.

Suitable binders, contemplated for use herein, include common yellow dent starch, modified starches (e.g., hydroxypropyl addition, ethoxylation, acetylation, acid thinning etc.), sugars (e.g., sucrose, dextrose, fructose, lactose etc.), maltodextrin, polyvinylpyrolidine (PVP), polyethylene glycol (PEG), xanthum gum, gum arabic, acacia gum, alginate, carrageenin, waxes (e.g., carnuba, beeswax, paraffin and blends thereof), high melting point surfactants (e.g., mp between 40 and 80° C.).

Proteins that are within the scope of the present invention include pharmaceutically important proteins such as hormones or other therapeutic proteins and industrially important proteins such as enzymes. In a preferred embodiment, any enzyme or combination of enzymes may be used in the present invention. Preferred enzymes include those enzymes capable of hydrolyzing substrates, e.g. stains. Preferred enzymes known as hydrolases may be used and include, but are not limited to, proteases (bacterial, fungal, acid, neutral or alkaline), amylases (alpha or beta), lipases, cellulases and mixtures thereof. Particularly preferred enzymes are subtilisins and cellulases. Exemplary subtilisins are described in U.S. Pat. No. 4,760,025,EP Patent 130 756 B1 and PCT Application WO 91/06637,which are incorporated herein by reference. Exemplary cellulases include Multifect L250™ and Puradax™, commercially available from Genencor International. Other enzymes that can be used in the present invention include oxidases, transferases, dehydratases, reductases, hemicellulases and isomerases.

Among the places in the granule where the enzyme can be loaded include: centrally within the core or seed material (e.g., in a layer around a centrally located seed particle); intermixed (e.g., homogeneously) with the core or seed material; as a layer over the core or seed material, or surrounding, the core or seed material; as a layer separated from the core material by one or more other layers; as well as any combination thereof.

Plasticizers may be used to protect or facilitate a particular layer or can be used to protect the granule as a whole. Suitable plasticizers useful in the present invention include polyols such as glycerol, propylene glycol, polyethylene glycol (e.g., low MW PEGs), urea, or other known plasticizers. Suitable anti-agglomeration agents include fine insoluble or sparingly soluble materials such as talc, $TiO_2$, clays, amorphous silica, magnesium stearate, stearic acid and calcium carbonate. Thus, plasticizers and anti-agglomeration agents can be included, for example, in an overcoating applied to a granule.

A barrier layer can be used to slow or prevent the diffusion of substances that can adversely affect the protein or enzyme in the granule. The barrier layer can be made up of a barrier material and can be coated over the core and/or over an enzyme layer that surrounds the core; and/or the barrier material can be included in the core. Suitable barrier materials include, for example, starch, inorganic salts or organic acids, or salts. In one embodiment, the barrier layer comprises starch and a binder (e.g., sucrose) coated over an enzyme-containing core.

As noted above, the granules of the present invention can comprise one or more coating layers any of which may be produced according to the method of the invention. For example, such coating layers may be one or more intermediate coating layers or such coating layers may be one or more outside coating layers or a combination thereof, any of which may be produced with the addition of an antifoam agent. In addition, coating layers may be added and may serve any of a number of functions in a granule composition, depending on the end use of the enzyme granule. For example, coatings may render the enzyme resistant to oxidation by bleach, prevent enzyme leakage, bring about the desirable rates of dissolution upon introduction of the granule into an aqueous medium, or provide a barrier against ambient moisture in order to enhance the storage stability of the enzyme and reduce the possibility of microbial growth within the granule.

Suitable coatings include water-soluble or water dispersible film-forming polymers such as polyvinyl alcohol (PVA), polyvinyl pyrrolidone (PVP), cellulose derivatives such as methylcellulose (MC), hydroxypropyl methylcellulose (HPMC), hydroxyethyl cellulose, carboxymethyl cellulose, hydroxypropyl cellulose, polyethylene glycol, polyethylene oxide, gum arabic, xanthan, carrageenin, chitosan, latex polymers, and enteric coatings. Furthermore, coating agents may be used in conjunction with other active agents of the same or different categories.

Suitable PVAs for incorporation in the coating layer(s) of the granule include partially hydrolyzed, fully hydrolyzed and intermediately hydrolyzed PVAs having low to high degrees of viscosity. Preferably, the outer coating layer comprises partially hydrolyzed PVA having low viscosity. Other vinyl polymers which may be useful include polyvinyl acetate and polyvinyl pyrrolidone. Useful copolymers include, for example, PVA-methylmethacrylate copolymer and PVP-PVA copolymer and enteric co-polymers such as those sold under the trade name Eudragit® (Rhone Poulenc).

The coating layers of the present invention may further comprise one or more of the following: plasticizers, extenders, lubricants, pigments, and optionally additional proteins such as enzymes. Suitable plasticizers useful in the coating layers of the present invention are plasticizers including, for example, polyols such as sugars, sugar alcohols, or polyethylene glycols (PEGs), urea, glycol, propylene glycol or other known plasticizers such as triethyl citrate, dibutyl or dimethyl phthalate or water. Suitable pigments useful in the coating layers of the present invention include, but are not limited to, finely divided whiteners such as titanium dioxide or calcium carbonate or colored pigments and dyes or a combination thereof. Preferably such pigments are low residue pigments upon dissolution. Suitable extenders include sugars such as sucrose or starch hydrolysates such as maltodextrin and corn syrup solids, clays such as kaolin and bentonite and talc. Suitable lubricants include nonionic surfactants such as Neodol, tallow alcohols, fatty acids, fatty acid salts such as magnesium stearate and fatty acid esters.

Adjunct ingredients may be added to any of the layers of the enzyme containing granules of the present invention. Adjunct ingredients may include: metallic salts; solubilizers; activators; antioxidants; dyes; inhibitors; binders; fragrances; enzyme protecting agents/scavengers such as ammonium sulfate, ammonium citrate, urea, guanidine hydrochloride, guanidine carbonate, guanidine sulfamate, thiourea dioxide, monoethanolamine, diethanolamine, triethanolamine, amino acids such as glycine, sodium glutamate and the like, proteins such as bovine serum albumin, casein and the like etc.; surfactants including anionic surfactants, ampholytic surfactants, nonionic surfactants, cationic surfactants and longchain fatty acid salts; builders; alkalis or inorganic electrolytes; bleaching agents; bluing agents and fluorescent dyes and whiteners; enzyme stabilizers such as betaine, peptides and caking inhibitors.

Preferably, the granules produced in accordance with the present invention are roughly round, or spherical, in shape.

The granules described herein may be made by methods known to those skilled in the art of particle generation, including but not limited to marumerization, drum granulation, fluid-bed spray-coating, pan-coating, or other suitable process, or combinations of such techniques. Several exemplary methods for producing the particulate compositions and granules of the invention are described next.

In one preferred embodiment of fluid bed spray coating, a seed particle is charged into a fluid bed coater and fluidized. A coating solution consisting of a binder or binder system along with a non-porous or minimally porous, low-density material (e.g., hollowspheres) and optionally including other low-density materials is sprayed onto the seed to generate a particulate or core. Also, the non-porous or minimally porous, low-density material (and other low-density materials, if applicable) may be added dry along with application of a binder spray in either a pan or fluidized bed coater. After the core is generated, an enzyme can be layered onto the core. Optionally, this may be followed by other layers whose purpose can be, for example, buffering, providing a protective barrier, bulking, providing another value/performance added material. Finally, a cosmetic coating can be applied to provide aesthetics and protection from the environment. If desired, the entire process can be performed in a pan coater. Moreover, any part of this process can be performed in either a pan coater or a fluidized bed coater.

Suitable seed particles for use in the just-described method include, for example, a sugar crystal, salt crystal, non-pareil, a prill with an acceptable melting point, an extruded particulate, a particulate from a drum granulation, etc.

In another embodiment for forming a granule, a core or seed material can be blended in a solution consisting of melted components and little or no water or other solvent. This solution can be fed to a spinning disc, centrifugal nozzle or any other type of prilling device which is used to generate spherical particles of sizes between 50 and 3000 um. The prills are generated at some height above a collection area which allows them to cool and harden as they fall. Alternatively, a counter-current chilling air-stream may be used to facilitate prill hardening and control particle velocities. Optionally, enzyme may be added to the hot-melt solution in the form of a dry powder, enzyme-crystal slurry or paste, enzyme precipitate slurry or paste or in a solubilized form in either an aqueous or non-aqueous solvent. In any of the above enzyme additions, solvent of liquid carrier concentration in the hot-melt cannot rise to above a level where spheroidal, non-friable prills are no longer formed. These enzyme prills can then be cosmetically coated, as an option.

In a further embodiment, enzyme granules of the present invention are made by an extrusion method by adding the core material to the dry blend and then processing as described in, for example, U.S. Pat. No. 5,739,091, incorporated herein by reference.

In yet another embodiment, low-density enzyme granules of the present invention are made by a drum granulation method by adding the core material to the dry blend and processing as described in, for example, in PCT WO 90/09440, incorporated herein by reference.

In still a further embodiment, the core material can be blended into a solution/slurry that is used to produce the core of a microencapsulated product. This solution can be sprayed along with a shell solution through a binary phase nozzle, where the core solution exits through the inner liquid port and the shell solution exits through the outer concentric liquid port, and atomized via centrifugal force, mechanical vibration, jet cutting, sonics, cross shear from a liquid or gas stream, electromagnetic field, etc. Depending on the shell, the microencapsulate can be collected in a liquid based collection bath, a solid media that facilitates free-flow of the product or in static or countercurrent air stream that allows hardening/setting up of the product before it reaches a collection vessel. Optionally, the microencapsulate can be dried and/or cosmetically coated.

The shell can be composed of any material(s) that efficiently entrap the inner core and provide enough rigidity so that the microcapsule can be handled in relevant applications without significantly deforming, agglomerating, decomposing or in other ways becoming non-utile.

The granules described herein may be made by methods known to those skilled in the art of enzyme granulation, including pan-coating, fluid-bed coating, fluid-bed agglomeration, prilling, disc granulation, marumerization, spray drying, extrusion, centrifugal extrusion, spheronization, drum granulation, high shear agglomeration, or combinations of these techniques.

The following examples are representative and not intended to be limiting. One skilled in the art could choose other proteins, protein cores, enzymes, enzyme cores, seed particles, methods and coating agents based on the teachings herein.

EXAMPLES

Example 1

In this example, a granule comprising a seed and three layers was produced wherein antifoaming agent was added to the enzyme layer. A control was prepared with no antifoam added and the dust levels were compared. To produce the granules, 1.0 kg of sucrose crystals was sieved to between 35 and 50 mesh were charged into Glatt 3 fluid bed coater and fluidizer. 1.6 Kg of an aqueous protease solution with 15.5% total dry solids was added to 3.27 kg of an aqueous solution containing 0.84 kg of sucrose and 0.84 kg of cornstarch. Lot #2 differed from lot #1 by the addition of 47 grams of the antifoaming agent ethylene oxide propylene oxide co-polymer (Mazu™ DF204) to the above described formulation. The protease solution was sprayed onto the sucrose seed crystal under the following conditions:

| Fluid feed rate | 43 gram/min |
| Atomization pressure | 20 PSI |
| Product temp. | 45° C. |
| Inlet air flow | 100 CFM |

The coated particles were then coated with an aqueous solution containing 1.6 kg (50% w/w) of magnesium sulfate heptahydrate. This coating was applied under the following conditions:

| Fluid feed rate | 50 gram/min |
| Atomization pressure | 30 PSI |
| Product temp. | 45° C. |
| Inlet air flow | 100 CFM |

The magnesium sulfate coated particles were then cosmetically coated with 3.5 kg of an aqueous solution containing 267 g (6% w/w) titanium dioxide, 111 g (2.5% w/w) methylcellulose (Methocell, available from the Dow Company), 111 g (2.5%) Purecote B790 (available from Grain Products Corp), 67 g (1.5% w/w) neodol 23/6.5, and 74 g (1.7% w/w) of polyethylene glycol at a MW of 600. The cosmetic coating was applied under the following conditions:

| Fluid feed rate | 43 gram/min |
|---|---|
| Atomization pressure | 40 PSI |
| Product temp. | 45° C. |
| Inlet air flow | 100 CFM |

The results show that adding antifoaming agent to the enzyme layer of the granule reduces the dust levels in both the Heubach and Elutriation tests.

| LOT #1 | LOT #2 |
|---|---|
| \multicolumn{2}{Seed:} | |
| 25% sucrose | 25% sucrose |
| \multicolumn{2}{Enzyme Layer} | |
| 17.8% Corn Starch | 17.8% Corn Starch |
| 17.8% sucrose | 17.8% sucrose |
| 5.2% UF conc. Solids | 5.2% UF conc. Solids |
|  | 1% antifoam |
| \multicolumn{2}{2nd Layer} | |
| 20% MgSO4•7H2O | 20% MgSO4•7H2O |
| \multicolumn{2}{3rd Layer} | |
| 2.5% Purecote 790 | 2.5% Purecote 790 |
| 2.5% Methyl cellulose A15 | 2.5% Methyl cellulose A15 |
| 1.5% Neodol | 1.5% Neodol |
| 1.7% PEG 600 | 1.7% PEG 600 |
| 6.0% TiO2 | 6.0% TiO2 |

| TEST RESULTS | Heubach mg/pad | Elutriation Dust GU/60 g |
|---|---|---|
| Lot #1 | 7.8 | 1.2 (0.014 µg/60 g) |
| Lot #2 | 1.7 | 0.23 (0.0026 µg/60 g) |

Example 2

In this experiment, antifoaming agent was added to the first layer (comprising enzyme) and the second layer (a coating layer comprising corn starch, titanium dioxide and neodol) and the dust potential was compared to a granule made without antifoam.

Lot 1 was prepared as follows:

25 kg sucrose crystals sieved to between 35 and 50 mesh were charged into Deseret 60 fluid bed coater and fluidizer. 39 Kg of an aqueous protease solution with 15.5% total dry solids was added to 63 kg of an aqueous solution containing 22.5 kg of sucrose and 22.5 kg of cornstarch.

Lot 2 was prepared as follows:

25 kg sucrose crystals sieved to between 35 and 50 mesh were charged into Deseret 60 fluid bed coater and fluidizer. 39 Kg of an aqueous protease solution with 15.5% total dry solids was added to 63 kg of an aqueous solution containing 21.3 kg of sucrose and 21.3 kg of cornstarch and 1.2 kg (1% w/w) of Mazu DF204.

Protease solutions were sprayed onto the sucrose crystals under the following conditions:

| Fluid feed rate | 750 gram/min |
|---|---|
| Atomization pressure | 75 PSI |
| Product temp. | 45° C. |
| Inlet air flow | 1200 CFM |

The coated particles were then coated with an aqueous solution containing 82.4 kg (40% w/w) of 11.7 kg (10.2% w/w) of sucrose, 11.7 kg of cornstarch, 6.9 kg (6.0% w/w) titanium dioxide and 1.5 kg (1.3% w/w) of neodol. Lot #2 had 1.2 kg (1%) mazu added to its spray solution. This coating was applied under the following conditions:

| Fluid feed rate | 1200 gram/min |
|---|---|
| Atomization pressure | 60 PSI |
| Product temp. | 45° C. |
| Inlet air flow | 1200 CFM |

The coated particles were then cosmetically coated with 65.8 kg of an aqueous solution containing 2.94 kg (2.5% w/w) hydroxymethylcellulose E15, and 353 g (0.3% w/w) of polyethylene glycol at a MW of 600. The cosmetic coating was applied under the following conditions:

| Fluid feed rate | 750 gram/min |
|---|---|
| Atomization pressure | 75 PSI |
| Product temp. | 45° C. |
| Inlet air flow | 1200 CFM |

As shown below, adding Mazu as an antifoam agent to layers 1 and 2 of the granule reduces the Heubach total dust levels.

| LOT #1 | LOT #2 |
|---|---|
| \multicolumn{2}{Seed:} | |
| 25% sucrose | 25% sucrose |
| \multicolumn{2}{Enzyme Layer} | |
| 19.6% Corn Starch | 18.6% Corn Starch |
| 19.6% sucrose | 18.6% sucrose |
| 5.3% UF conc. Solids | 5.3% UF conc. Solids |
|  | 1% antifoam |
| \multicolumn{2}{2nd Layer} | |
| 10.2% corn starch | 10.2% corn starch |
| 10.2% sucrose | 10.2% sucrose |
| 1.3% Neodol | 1.3% Neodol |
| 6.0% TiO2 | 6.0% TiO2 |
|  | 1% antifoam |
| \multicolumn{2}{3rd Layer} | |
| 2.5% HPMC E15 | 2.5% HPMC E15 |
| 0.3% PEG 600 | 0.3% PEG 600 |

| TEST RESULTS | Heubach mg/pad |
|---|---|
| Lot #1 | 8.0 |
| Lot #2 | 0.1 |

Example 3

In this example, antifoam was added to the third layer of a granule and compared to a granule prepared with no anti-foaming agents.

25 kg sucrose crystals were sieved to between 35 and 50 mesh were charged into Deseret 60 fluid bed coater and fluidizer. 54 Kg of an aqueous protease solution with 21.4% total dry solids was added to 73 kg of an aqueous solution containing 20.6 kg of sucrose and 20.6 kg of cornstarch.

Protease solutions were sprayed onto the sucrose under the following conditions:

| | |
|---|---|
| Fluid feed rate | 750 gram/min |
| Atomization pressure | 75 PSI |
| Product temp. | 45° C. |
| Inlet air flow | 1200 CFM |

The coated particles were then coated with an aqueous solution containing 82.4 kg (40% w/w) of 11.7 kg (10.2% w/w) of sucrose, 11.7 kg of cornstarch, 6.9 kg (6.0% w/w) titanium dioxide and 1.5 kg (1.3% w/w) of neodol. This coating was applied under the following conditions:

| | |
|---|---|
| Fluid feed rate | 1200 gram/min |
| Atomization pressure | 60 PSI |
| Product temp. | 45° C. |
| Inlet air flow | 1200 CFM |

Lot 1 coated particles were then cosmetically coated with 65.8 kg of an aqueous solution containing 2.94 kg (2.5% w/w) hydroxymethylcellulose E15,and 353 g (0.3% w/w) of polyethylene glycol at a MW of 600.Lot #2 had 1.2 kg (1% w/w) Mazu DF204 added to the spray 3 solution. The cosmetic coating was applied under the following conditions:

| | |
|---|---|
| Fluid feed rate | 750 gram/min |
| Atomization pressure | 75 PSI |
| Product temp. | 45° C. |
| Inlet air flow | 1200 CFM |

As shown below, adding Mazu antifoam to the 3$^{rd}$ layer of the D-type granule reduces the Heubach total dust levels.

| LOT #1 | LOT #2 |
|---|---|
| Seed: | |
| 25% sucrose | 25% sucrose |
| Enzyme Layer | |
| 18.2% Corn Starch<br>18.2% sucrose<br>5.3% UF conc. Solids | 18.2% Corn Starch<br>18.2% sucrose<br>5.3% UF conc. Solids |
| 2nd Layer | |
| 10.2% corn starch<br>10.2% sucrose<br>1.3% Neodol<br>6.0% TiO2 | 10.2% corn starch<br>10.2% sucrose<br>1.3% Neodol<br>6.0% TiO2 |
| 3rd Layer | |
| 2.5% HPMC E15<br>0.3% PEG 600 | 2.5% HPMC E15<br>0.3% PEG 600<br>1.0% Mazu DF204 |

-continued

| TEST RESULTS | Heubach mg/pad |
|---|---|
| Lot #1 | 12.3 |
| Lot #2 | 1.4 |

What is claimed is:

1. A granule for use in solid formulations comprising: a core; an admixture of an allergenic agent and antifoaming agent surrounding the core; wherein the granule has at least 10% less dust as measured by a Heubach test than a granule without the antifoaming agent prepared by an identical process, wherein the antifoaming agent comprises a copolymer of ethylene oxide and propylene oxide, and wherein the antifoaming agent comprises about 0.25%-10% w/w of the granule.

2. The granule of claim 1 further comprising a coating surrounding the admixture of the allergenic agent and antifoaming agent layer.

3. The granule of claim 1 further comprising a barrier layer between the allergenic agent and antifoaming agent surrounding the core and the coating.

4. The granule of claim 1 wherein the admixture of the allergenic agent and antifoaming agent further comprises one or more barrier materials.

5. The granule of claim 2 wherein the coating comprises at least one of a plasticizer, an anti-agglomeration agent, a film-forming polymer, an extender, a lubricant, and a pigment.

6. The granule of claim 2 wherein the coating comprises at least one plasticizer and at least on anti-agglomeration agent.

7. The granule of claim 2 wherein the coating comprises an antifoaming agent.

8. The granule of claim 2 wherein the coating comprises at least one inner coating and an outer coating.

9. The granule of claim 1 wherein the allergenic component comprises an enzyme or protein.

10. A granule for use in solid formulations comprising: a core particle; an admixture of an allergenic component and antifoaming agent surrounding the core particle; a coating surrounding the admixture, the coating comprising an antifoaming agent and at least one barrier material, wherein the granule has at least 10% less dust as measured by a Heubach test than a granule without the antifoaming agent prepared by an identical process, wherein the antifoaming agent comprises a copolymer of ethylene oxide and propylene oxide, and wherein the antifoaming agent comprises about 0.25%-10% w/w of the granule.

11. The granule of claim 10 further comprising an outer coating surrounding the coating.

12. The granule of claim 10 wherein the admixture further comprises at least one barrier material and the coating further comprises a lubricant and a pigment.

13. The granule of claim 11 wherein the outer coating comprises a plasticizer and a film-forming polymer.

14. The granule of claim 10 wherein the allergenic component comprises an enzyme or protein.

15. A granule for use in solid formulations comprising: a core; an allergenic component surrounding the core; a coating surrounding the allergenic component, the coating comprising at least one barrier material, and an outer coating comprising at least an anti-foaming agent, wherein the granule has at least 10% less dust as measured by a Heubach test than a granule without the antifoaming agent prepared by an identical process, wherein the antifoaming agent comprises a copolymer of ethylene oxide and propylene oxide, and wherein the antifoaming agent comprises about 0.25%-10% w/w of the granule.

16. The granule of claim 15 wherein the coating further comprises two barrier materials, a lubricant and a pigment.

17. The granule of claim 15 wherein the outer coating further comprises a film-forming polymer and a plasticizer.

18. The granule of claim 15 wherein the allergenic component comprises an enzyme or protein.

* * * * *